Figure 1:
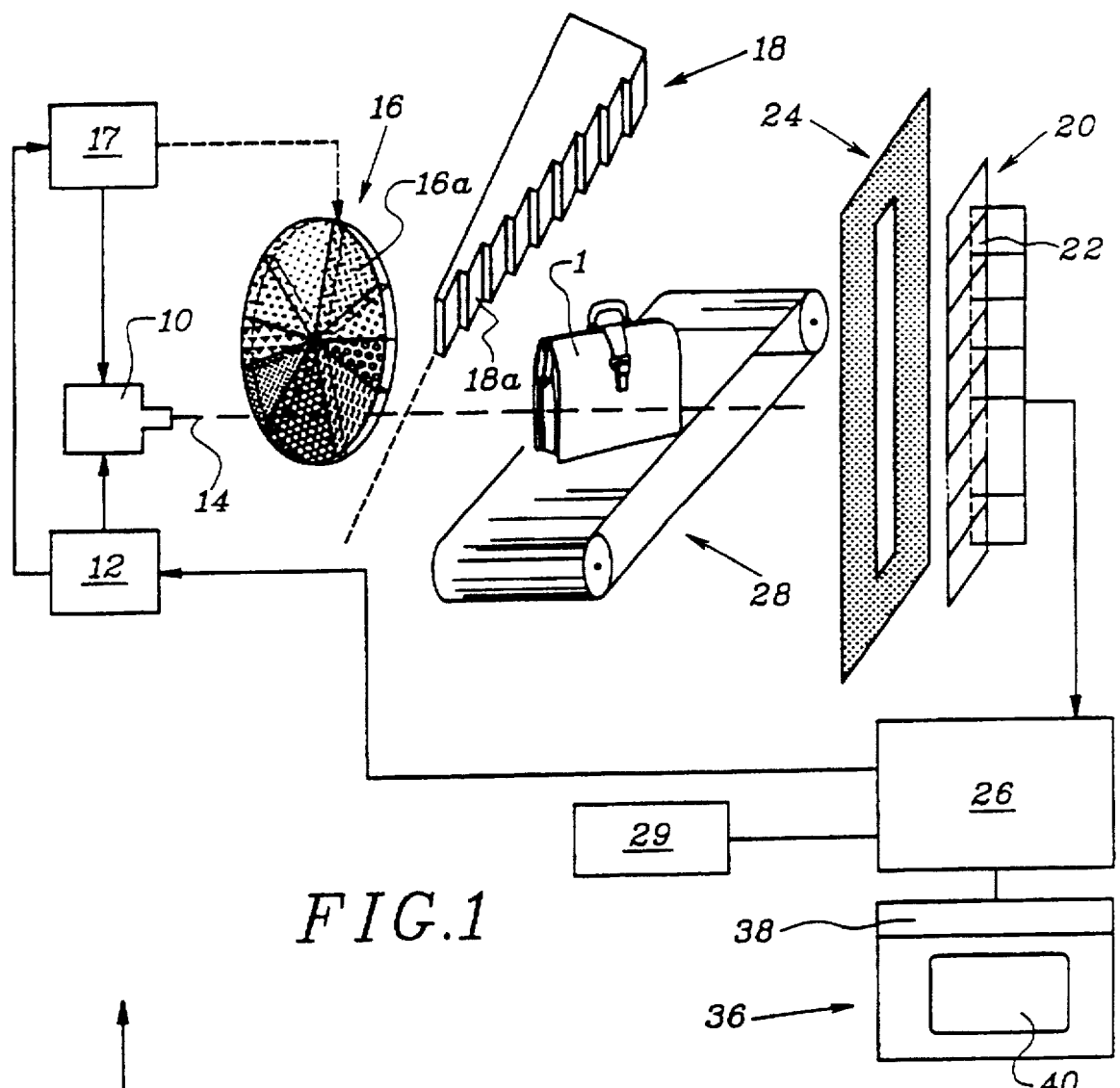

United States Patent [19]

Maitrejean et al.

[11] Patent Number: 5,768,334
[45] Date of Patent: Jun. 16, 1998

[54] METHOD AND DEVICE FOR IDENTIFYING DESIGNATED MATERIALS IN THE COMPOSITION OF AN OBJECT

[75] Inventors: Serge Maitrejean; Didier Perion, both of Paris, France

[73] Assignee: Europ Scan, Rungis Cedex, France

[21] Appl. No.: 556,909

[22] PCT Filed: May 16, 1994

[86] PCT No.: PCT/FR94/00580

§ 371 Date: Jul. 12, 1996

§ 102(e) Date: Jul. 12, 1996

[87] PCT Pub. No.: WO94/28442

PCT Pub. Date: Dec. 8, 1994

[30] Foreign Application Priority Data

May 28, 1993 [FR] France .................... 93 06448

[51] Int. Cl.[6] .................................................. G01N 23/06
[52] U.S. Cl. .................................................. 378/53; 378/57
[58] Field of Search ................................ 378/53, 56, 57

[56] References Cited

U.S. PATENT DOCUMENTS 3,673,394  6/1972  Hartmann ........................ 364/560
4,031,545  6/1977  Stein et al. ...................... 378/57
5,335,260  8/1994  Arnold ............................ 378/207

*Primary Examiner*—David P. Porta
*Assistant Examiner*—David Vernon Bruce
*Attorney, Agent, or Firm*—Lowe, Price, LeBlanc & Becker

[57] ABSTRACT

The method comprises the following stages: first the attenuation function of at least three reference materials are determined across a wide x-ray spectrum and projection functions ($F_{p1}$, $F_{p2}$, $F_{p3}$, $F_{p4}$) forming a base are derived therefrom, then the attenuation function in said x-ray spectrum of at least one target material is determined and the attenuation function of each target material is projected onto said base; further, for each point of the object (1), the attenuation function of the object (1) is determined in said x-ray spectrum and projected onto said base, and the projections so obtained are compared with the projection from each target material and from this comparison an inference is made whether at least one target material enters the constitution of the object (1) at the point of inspection.

Application: luggage inspection and control.

18 Claims, 2 Drawing Sheets

METHOD AND DEVICE FOR IDENTIFYING DESIGNATED MATERIALS IN THE COMPOSITION OF AN OBJECT

The present invention concerns a method of identifying specific materials in an objects composition/constitution and a device/apparatus to implement this method. The invention applies in particular to detecting specific materials such as explosives or drugs.

The patent document WO 92 02892 describes several procedures and apparatus for inspecting luggage and for the detection of specific materials. The object being inspected is exposed to an x-ray beam providing either of two different (high and low) energies. The beam attenuation in the object is measured. Accordingly a pair of attenuations are obtained at each image point, one of the high-energy range and the other for the low-energy range.

Moreover there are preliminary measurement& These cost in determining pairs of attenuations (one for the high, the other for the low energy range) for a large number of samples representative of the specific material(s) being looked for in the object. With respect to each type of specific material, the samples are in the form of different specific-material thicknesses in turn covered with different thicknesses of a coating material. All these pairs of reference attenuations are classified in a stored table. They are also related to a parameter P equal to the thickness of the specific material for the sample being considered.

When the object being examined is exposed to the x-ray beam, then the measured pair of attenuations at one image point will be compared with the pairs of attenuations recorded in the table.

A value of the parameter P is deduced by interpolation. By correlating at least one of the attenuations of the measured pair, for instance that in the high-energy range, with the value of P, it is possible to infer whether the object does contain some amount of the specific material at the test point. Detection errors and hence false alarms are reduced by comparing the different image points with their neighbors.

This procedure incurs major drawbacks:

Two measurements art carried out for each image point, one for the high energies, the other for the low ones. These two measurements are substantially independent and allow deriving two independent data at each point. These two independent data are used in inferences on the chemical constitution of the object being inspected.

These two data are independent because two predominant physical effects, namely the photoelectric and the Compton effects may take place when an X photon interacts with the material. However other independent data also are accessible because other independent physical effects occur during this sort of interaction Accordingly the procedure advocated in WO 92 02892 does not fully utilize all the latent information in an interaction between an X photon and a material.

In order to compensate for the restriction to two independent data in securing information on the inspected object's chemical constitution, the prior art recommends using correlation between the attenuated measurements and a parameter P corresponding to tabulated attenuation values. These tabulated attenuation values must be stored in very large numbers in order to preclude spurious interpretation. Nevertheless, however large the number of tabulated pairs of attenuations, this highly indirect method will not eliminate the danger of false alarms on one hand nor on the other will it preclude detection failure when the target material is present.

The x-ray beam's characteristics (intensity, spectrum, energy . . . ) vary rapidly and markedly with time.

The attenuation pairs recorded in the table and produced by calibrating with a beam of specified properties depend on these properties and no longer will be applicable as references with a beam of different properties.

As a result, it may happen, on account of beam modification, that specific-material identification in fact will be a false alarm and, even more seriously, that on the other hand the system may overlook a specified, that is a target material inside the object The latter case may entail fatal consequences if such a specified material is an explosive inside luggage It is possible to compensate variation in beam properties using calibrations carried out at regular intervals and close enough to one another to preclude beam drifts from affecting detection. However considering the way this procedure is carried out, calibration entails measuring all the attenuation pairs in the table and then reestablish their correlations with the values of the parameter P.

This means, tangibly, that different thickness of the target material, and different cladding thicknesses, are made to pass into the beam path. The interpolation of an attenuation pair between the tabulated pairs is the more accurate the larger the number of tabulated pairs. Consequently, updating the tabulated attenuation pairs demands much time, but this requirement is incompatible with continuous operation of the apparatus.

It is true that the calibrations may be subdivided and the calibration measurements may be carried out during the apparatus idle times, that is, for the case of luggage inspection, in the interval between two consecutive pieces of luggage passing by. Nevertheless, when the number of samples is high, where a sample corresponds to a given thickness of specified material together with a given cladding thickness, and this is the case to achieve adequate accuracy, the time between two refreshments of a tabulated pair of attenuations is substantial and the danger of error cannot be ignored.

The object of the present invention is palliation of the cited drawbacks. For that purpose the invention recommends using a wide-spectrum attenuation function rather than two measurements of attenuation of which one corresponds to a low-energy range and the other to a high-energy range.

In this manner at least three independent data may be deduced to chemically characterize an object In theory, the attenuation function allows a large amount of independent data, but in practice it happens that the physical phenomena of lesser probability than the photoelectric or Compton effects that are present during the interaction of the X photons with matter are in fact partly correlated to one another and thereby restrict the amount of information that the attenuation measurements may provide.

In particular, the present invention concerns a method for identifying target materials in an object's constitution. This method comprises the following stages:

A. First to determine the attenuation function over a wide x-ray spectrum of at least three reference materials and deducing therefrom base functions, B. In the course of a second preliminary stage, to determine the attenuation function in said x-ray spectrum for at least one target material and to place the attenuation function of each target material in said base, C. As regards each point in the object:
   determining the object's attenuation Fission across said x-ray spectrum integrate said attenuation function into said base, compare the integrations so obtained with the projections of each target material and deduce from this comparison if at least one target material is present in the constitution of the object at the point being checked.

Advantageously the x-ray spectrum runs in a range at least from 30 Kev to 100 Kev.

Preferably the object's attenuation function, further the reference-material attenuation functions and the target-material attenuation functions all are expressed in terms of an independent variable u bijectively related to the x-ray energy.

This variable u may be the attenuation of a fixed thickness of a calibration material This calibration material advantageously evinces an effective atomic a number Z in a range from 5 to 26.

Preferably the projection functions are mutually orthogonal.

In a particular embodiment of the invention, the projection functions are eigenfunctions associated with eigenvalues determined from diagonalizing a matrix constituted of scalar products of the reference-materials' attenuation functions.

Advantageously, in this embodiment and during a preliminary stage, a set of projection coefficients resulting from the projection of the target-materials' attenuation functions onto said base is determined for each target material, and, said eigenvalues being arranged in decreasing order from each set of projection coefficients, a set of comparison coefficients is derived for the target materials by dividing each projection coefficient of the particular set by the coefficient of the particular set that corresponds to the projection on that projection function associated with the largest of the eigenvalues, said sets of comparison coefficients allowing to infer whether at least one target material is present in the constitution of the object.

If the object being inspected is composed of a set of discrete bodies, an image of the body contours is taken, said contour being transition zones between different bodies, at each object point, and a set of projection coefficients resulting from the projection of object's attenuation function onto said base is carried out, variations in the sets of object projection coefficients inside the transition zones are determined, and, from said variations comparison coefficients with the variation coefficients of the target materials are derived.

Advantageously the effective atomic numbers of the reference materials are regularly spaced in a range from 3 to 30.

In that case and in preferred manner, a first reference material is selected from the materials with an effective atomic number from 3 to 7, a second reference material is selected from those materials evincing an effective atomic number from 7 to 10 and a third reference material is selected from those materials which evince an effective atomic number from 10 to 17, and a fourth reference material is selected from those materials with an effective atomic number from 17 to 30.

The first reference material may be polyethylene, the second material is teflon, the third reference material is Duralumin, the fourth reference material is iron.

The target materials may be explosives or drugs when the application is luggage inspection.

Furthermore the invention concerns an apparatus implementing a method as described above. This apparatus comprises:

means determining attenuation functions in a wide x-ray spectrum, said attenuation functions being expressed in terms of a variable, i.e. an independent variable u in bijective relation to the energy of the x-rays, processing means able to project attenuation functions onto a base-forming functions which were previously determined from the attenuation functions of at least three reference materials, conveyor means for an object to be analyzed that allow exposing this object to means determining an attenuation function, means for comparing the projections of the objects attenuation functions with previously implemented projections of at least one target material, inferring from this comparison whether at least one target material enters the object's constitution, and means to display at least one image of object by distinguishing those is points at which a target material enters the object's constitution.

Advantageously the apparatus of the invention comprises image processing equipment able to form contour images.

Preferably the means determining the attenuation functions comprise a target made of a calibration material and evincing different thicknesses, said target being displaceable at will in the x-ray beam.

In a first variation, the means determining the attenuation function comprise a source consecutively emitting an x-ray beam over several spectral levels and a strip of detectors wherein each detector responds to all spectral levels.

In another variation, the means determining an attenuation function comprise an x-ray beam generator for a wide and fixed spectrum and a stacked detector strip, each stack detector serving as a high-pass filter for the next and adjacent detector.

The method and apparatus of the invention offer may advantages relative to the state of the art Herein the comparison elements are attenuation functions (actually their projections onto base functions) of the target materials. The number of available independent data regarding the object's constitution is therefore at least equal to the number of data of the prior art. At least one additional datum is furthermore immediately accessible, and thereby system reliability and sensitivity is improved.

Once determined and recorded, these attenuation functions no longer undergo fluctuations. Calibration is much simplified as a result.

To compensate any drift in x-ray beam, it is enough to carry out attenuation measurements of the various thicknesses of the calibration material. Such measurements are very rapid (about 10 ms per measurement) and also they may be taken frequently, whereby any detection error from changes in the beam characteristics can be avoided.

Figure 2:
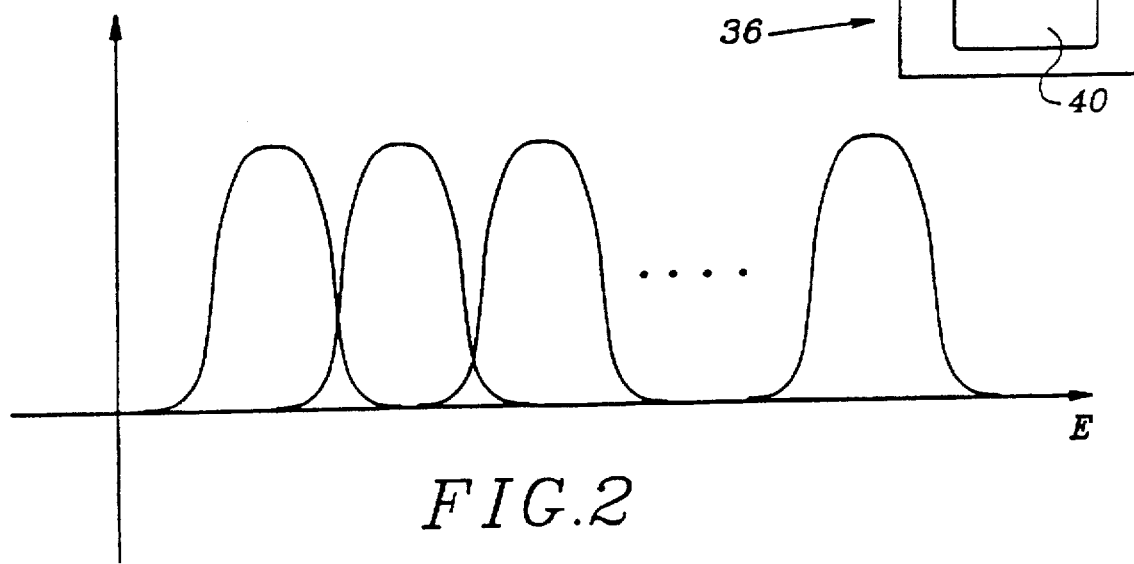
Figure 3:
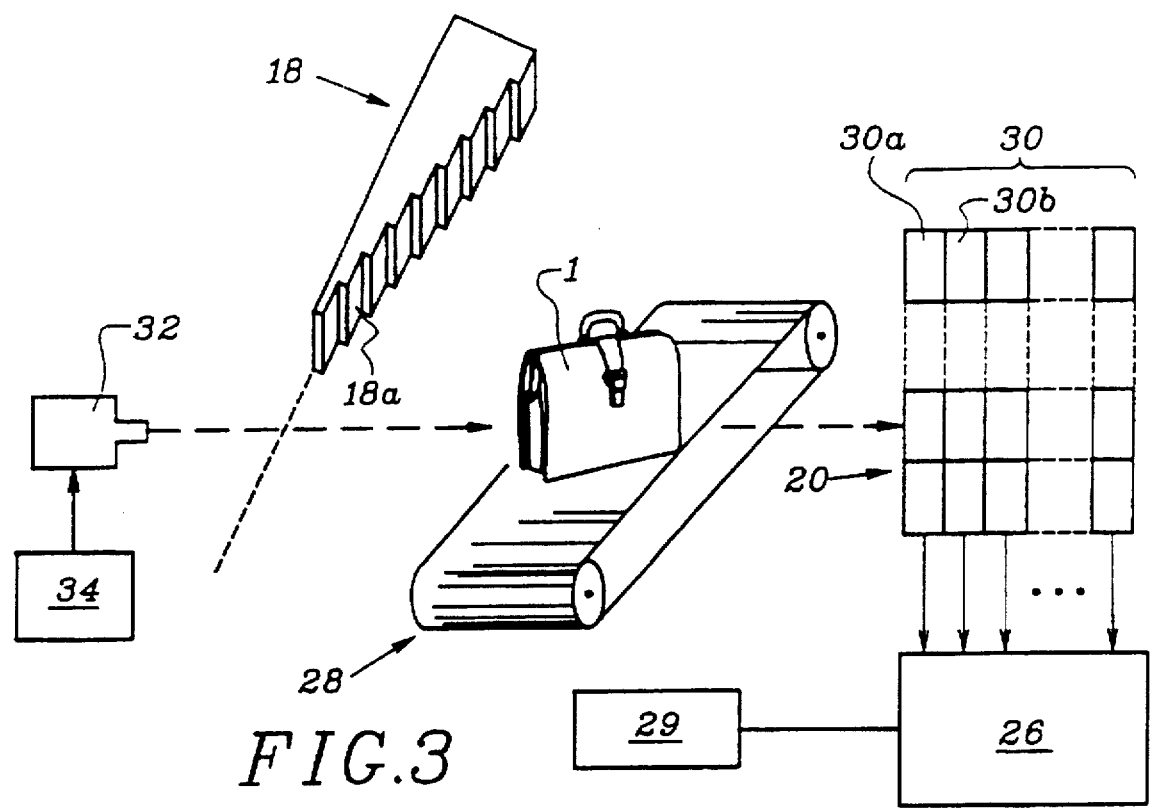
Figure 4:
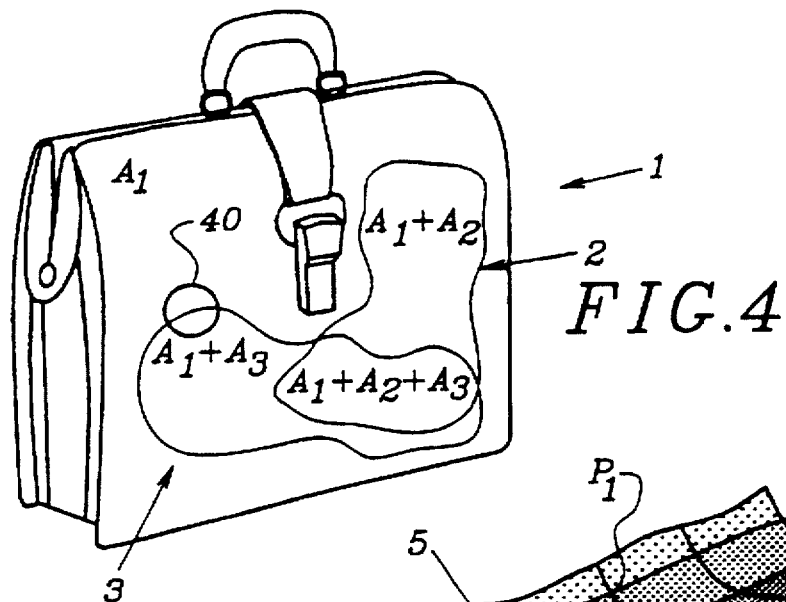
Figure 5:
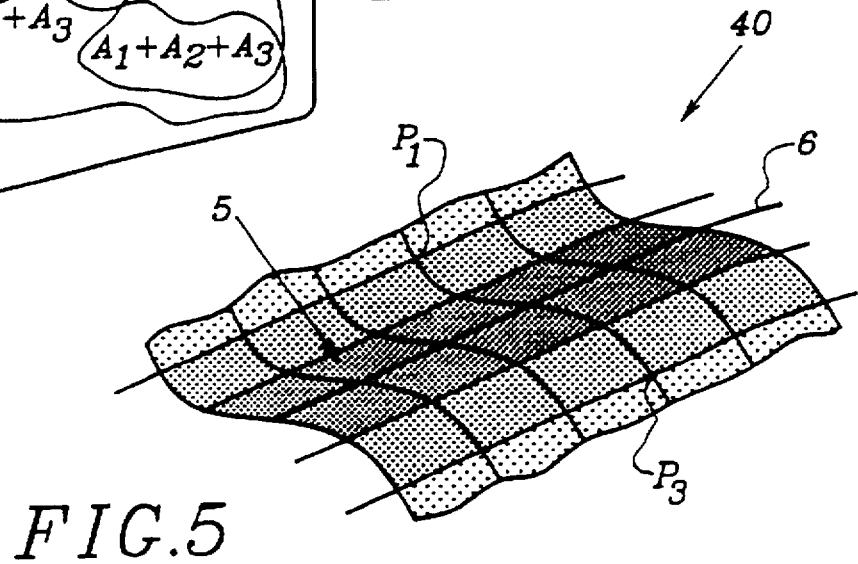

The present invention and its advantages are elucidated in the following illustrative and non-limiting description in relation to the attached drawings, FIG. 1 schematically shows apparatus implementing the method of the invention, FIG. 2 schematically shows a sequence of energy spectra used to measure transmission, FIG. 3 schematically shows an embodiment variation of apparatus implementing the method of the invention, FIG. 4 schematically shows an object's contour image, and FIG. 5 schematically shows an enlarged view of a portion of the image of FIG. 4.

Presently apparatus implementing a method of the invention will be described in relation to FIG. 1. This apparatus comprises means determining an attenuation function across a wide x-ray spectrum.

As shall be elucidated in the course of the description, said means determining an attenuation function are used several times:

A first time to measure the attenuation functions of reference materials. These attenuation functions in turn determine base functions. These measurements are taken once and for all during a preliminary stage.

A second time to measure the attenuation functions of target materials of which the presence is looked for in the constitution of the analyzed objects. These measurements also are taken once and for all during a second preliminary stage.

A third time to measure the attenuation functions at each point of the analyzed object.

Driven by a variable-voltage control system 12, an x-ray generator 10 emits a fan-beam 14 (the fan shape being produced in known manner using an omitted collimator in the form of a slit) of which the maximum energy varies in relation to the voltage applied to the x-ray generator. A system 16 allows moving in place different filters 16a in synchronization with the beam's energy variation. In the embodiment of FIG. 1, the filter-system 16 comprises a disk of which each portion corresponds to a different filter. These filters are high-pass and are known per se. One filter corresponds to each voltage applied to the x-ray generator.

The disk is set in rotation by a control system 17 connected to the control 12 to regulate synchronization.

Other filters may be used in equivalent manner, for instance sequentially arrayed filters may be translated into the beam path.

FIG. 2 shows the sequence of consecutively produced spectra when the disk rotates in relation to energy. The filters are selected in such a way that there is partial overlap of the consecutive spectra.

As regards the energy spectrum of the beam 14, each filter suppresses all energies lower than a filter-characteristic threshold. For each spectrum of FIG. 2, the portion of high energies corresponds to the maximum energy supplied by the generator 10 when the associated filter is placed in the beam path. In practice the energy spectra are not rigorously defined and their exact shape does not significantly affect measurement. On the other hand it is important that each spectrum's shape and intensity remain constant from the time of the reference measurements to the time of measuring the analyzed object.

The slight discontinuities in the sequence of the spectra do not affect the measurements either. However, to be innocuous, such discontinuities must be less than 5 Kev for the range from 20 Kev to 40 Kev and less than 10 Kev beyond.

Again referring to FIG. 1, it shows a stepped target or component 18. Each step corresponds to a material sample of a different thickness.

This component 18 is made of a calibration material of which the effective atomic number Z may be between 5 and 26. Illustratively the alloy known as Duralumin (a mixture composed of 95% Al, 4.5 % Cu and 0.5% Mn) of which the effective Z is about 13.5 is used.

In this embodiment, the thickness of the second step 18a is selected as the reference thickness. Obviously any other step also may be selected as the reference step. For Duralumin, the reference thickness may be chosen within a range from 1 to 5 mm, for instance being 4 mm.

In general, a number N of distinct calibration-material thicknesses and hence of N steps in the component 18 is required when N+1 spectra are used. A component 18 with 9 steps therefore matches apparatus using 10 energy spectra.

The component 18 may be placed at will by translation into the beam path. For clarity of exposition, the device implementing the translation of the component 18 is omitted from FIG. 1.

The component 18 also may assume other geometries equivalent to that of the shown component. Illustratively the component 18 may be a disk of which the portions evince the desired different thicknesses and one of which is cleared to allow free beam passage.

FIG. 1 shows that the apparatus includes a strip 20 of detectors 22 in the path of the beam 14. A strip 20 comprises about a thousand detectors 22 illustratively each consisting of a scintillator and a photodiode. The detector strip is placed to the rear of a collimating element 24 which may be a slit. The detector strip allows forming an image column, each detector 22 corresponding to one pixel of the image. The strip furthermore may be L-shaped.

At their outputs, the detectors 22 of the strip 20 are connected to the input of a processing system 26 such as a memory-equipped computer.

In conformity with the method of the invention, a first stage consists in analyzing the attenuation function of the object 1 at each of its points in an energy range at least from 30 to 100 Kev. Illustratively such a range may be from 20 to 150 Kev. In FIG. 1, the object 1 is illustrated as a suitcase.

During a preliminary stage wherein the object 1 is absent from the beam path, calibration measurements are carried out for each detector 22. These calibration measurements consist in measuring the intensities transmitted by the different thicknesses of the component 18 exposed to the test beam.

Initially this transmitted energy is measured for zero thickness, that is when the component 18 is absent from the beam path.

The system 26 controls the variable voltage and appropriate filtering of the beam by means of the filter-system 16. With the combination of voltage variation and appropriate filtering, the test beam 14 consecutively evinces N+1 different energy spectra. Illustratively N+1 may be 10.

One filter of the system 16 corresponds to each maximum energy of the beam to consecutively obtain the different energy spectra. Each variation of the maximum energy is synchronized with the emplacement of a new filter.

Each detector 22 measures the beam intensity of each spectrum and these measurements are stored by the processing system 26.

These measurements are repeated but the different thicknesses of the component 18 art consecutively placed in the beam path. Once these measurements have been stored in memory by the system 26, the component 18 is withdrawn from the beam path.

Accordingly apparatus calibration is very rapid. When the apparatus is in continuous use in monitoring luggage, the calibration may be repeated at each interval between two pieces of luggage.

Next the target 18 is withdrawn from the beam path and the object 1 to be analyzed is placed in said path. For that purpose the object is put on a belt-type conveyor 28. The object is translated slowly enough to allow forming consecutive image lines. Optimally, the object shall be displaced perpendicularly to the plane subtended by the longitudinal axis of the slit 24 and/or the strip 20 on one hand and on the other by the focal point of the x-ray generator tube.

With respect to one image line, the object 1 is consecutively exposed to each of the energy spectra produced by changing the maximum beam energy, in synchronization with insertion of appropriate filter. For each energy spectrum the intensity transmitted upon passage through the object is measured by the detectors 22 of the strip 20 and stored in memory.

Thanks to these measurements, the system 26 derives an analytical formula of the objects attenuation for each pixel. This attenuation is expressed in terms of an independent variable u in bijective relation with the energy E. In the presently described embodiment, u is the transmission of a given thickness of the component 18, for instance of the second step 18a, which shall be the reference.

If in this embodiment the component 18 is made of Duralumin of which the density (g/cm$^3$) is 2.7 and the thickness ep of the second step is 0.4 cm and chosen as reference, the variable u will be given by $u=e^{-att(E)(2.7)(0.4)}$ where att(E) is the attenuation per unit mass.

In general $u=e^{-att(E)(d)(ep)}$.

Defining the index j as the number of the spectrum to which n object is exposed, then j=1 corresponds to the lowest maximum-energy speck and the intensity $D_j$ trotted by the object is given by $$D_j = \int I_j(E) T_r(E) d(E) \quad (0).$$

or $$D_j = \int I_j(E) e^{-att(E)} dE \quad (1).$$

where $I_j(E)$ is the intensity of the jth energy spectrum in terms of the energy E, $T_r(E)$ and att(E) resp. are the transmission and attenuation functions here expressed in terms of E. By changing variables and replacing E with the parameter u.

$$D_j = \int I_j'(u) e^{-att'(u)} du \quad (2)$$

where $I_j'(u)$ is the intensity of the jth spectrum expressed in the value u of the parameter u and where att'(u) is the desired attenuation function.

The transmission function is expressed in terms of the parameter u. In a first stage, the system 26 will change variables as indicated and then it will approximate as follows: the object's transmission function is expressed as a finite polynomial expansion in powers of u, namely $$e^{-att'(u)} = \sum_{i=1}^{N} a_i u^{f(i)} \quad (3)$$

where i is the index from O to N.

In practice this is a highly accurate approximation.

The number (N+1) of expansion terms is less than or equal to the number of different energy spectra used for the transmission measurements. Consequently said number is less than or equal to the number N of reference-material thicknesses used in calibration, plus 1 (this corresponds to the absence of the component 18 in the beam). Thereby, each index i corresponds to a step number of the component 18, with index i =0 corresponding to zero thickness, that is, the component 18 is out of the beam path.

For each value of i, the expansion power f(i) in eq. 3 represents a ratio of one of the calibration-material thicknesses to the reference thickness. Advantageously these ratios are such that the powers f(i) increased by ½ constitute a geometric progression. This selection may be mathematically stated as $$f(i)+\tfrac{1}{2}=a^i[f(0)+\tfrac{1}{2}].$$

Moreover f(O) is selected to be zero so that i=0 shall correspond to the free beam path and hence to zero thickness, then $f(i)=(a^i-1)/2$.

Preferably too the reference thickness is included in the sequence. Thereby, if the second step was selected as the reference thickness, f(2)=1 and hence a=$\sqrt{3}$; the common ratio of the sequence is the square root of 3.

It can be shown that with this selection of the expansion powers, and hence of the step thicknesses, the expansion will be well-behaved.

In practice however, because of inevitable manufacturing tolerances, the f(i) do not assume rigorously the calculated values. However the minute deviations only trivially affect the true results.

It can be shown also that the intensity transmitted by the object 1 in spectrum j may be decomposed as $$D_j = \sum_{i=0}^{N} a_i C_{ji} \quad (4)$$

wherein the $C_{ji}$ terms for each spectrum j correspond to the intensity transmitted by the different thicknesses of the calibration material, i=0 corresponding to the zero thickness (the component 18 being out of the beam path).

In the equality (4), the terms $D_j$ and $C_{ji}$ are known from measurement only the $a_i$ coefficients being unknown. The number of calibration-material thicknesses (including the zero thickness) may be chosen less than or equal to the number of spectra and then the coefficients $a_i$ may be determined. In the presently ed embodiment, ten different energy spectra are used, the target 18 comprising nine steps, and the additional measurements carried out when the component 18 is out of the beam path must be added.

Consequently, during a subsequent stage, the system 26 will determine the $a_i$ coefficients using the values stored during calibration and the object's transmission measurements. Such determination may be carried out by any known procedure, for instance that of the least squares.

The attenuation Att is defined as $$Att=-Log(Tr)$$

where Tr is the transmission.

Once the coefficients have been determined, the system 26 substitutes their values into eq. (3) and then takes their naperian logs and multiplies by (−). In this manner the system 26 derives the attenuation function of the object 1 in terms of the parameter u.

FIG. 3 schematically shows an embodiment variation Instead of consecutively applying the different energy spectra of the beam 14, a wide and fixed spectrum measuring beam is used. For each pixel, the measurements of the intensity transmitted by the component 18 or the object I are carried out by a stack 30 of detectors 30a, 30b. . . . Each detector may consist of a scintillator and a photodiode.

The stacks 30 are juxtaposed to form a strip 20 which is shown in part in FIG. 3. Each detector operates as high-pass filter relative to the succeeding detectors. Thus each detector emits an electrical signal corresponding to the intensity for a portion of the wide energy spectrum. It is clear that, in the apparatus of FIG. 1, the objects being analyzed are exposed to a measuring beam consecutively evincing different energy spectra in such manner as to sweep the desired energy range, whereas in the apparatus of FIG. 3, the objects are exposed to a wide-spectrum measuring beam corresponding to the desired energy range, this wide spectrum being subsequently filtered by different detectors.

The apparatus of FIG. 3 comprises a measuring-beam generator 32. This generator 32 is connected to a fixed-voltage control 34 which ensures a wide energy spectrum in the measuring beam. The expression "wide energy beam"

denotes the full energy range to be analyzed, for instance the range from 20 Kev to 150 Kev.

As in the previous embodiment, the apparatus includes a stepped component 18 of specified thicknesses and made of a reference material. The component 18 may be displaced at will into the beam or it may be moved outside the beam path by a translation omitted from the drawing.

Each detector 30a, 30b . . . of the stack 30 is connected to the control and processing system 26. In this embodiment variation, the measurements of transmitted intensities of each sectional spectrum of the wide spectrum that are defined by the detector filters are carried out simultaneously. The processing performed by the system 26 to derive the attenuation function is similar to the processing already described above.

Using one such apparatus and the method described above, and during a preliminary stage following calibration and performed once and for all, the attenuation functions of at least three reference materials expressed in terms of u are determined.

The target materials that are being looked for in the constitution of the amazed object may be of any kind.

A range of effective atomic numbers for instance from 5 to 30 is selected and within this range reference numbers with effective atomic numbers Z regularly spaced apart are selected to cover this reference range.

The description below illustratively relates to four reference materials. However the invention is applicable when using at least two reference materials.

The first reference material evinces an effective Z number in a range from 2 to 7 and illustratively may be polyethylene with an effective Z about 5.3.

The second reference material comprises an effective Z number in the range from 7 to 10 and for instance may be teflon with an effective Z of about 8.

The third reference material evinces an effective Z number in the range of 10 to 17 and may be for instance Duralumin with an effective Z of about 13.5.

The fourth reference material evinces an effective Z number in the range of 17 to 30 and illustratively may be iron with an effective of Z of about 26.

The attenuation functions expressed in u of the target materials are determined once and for all during another preliminary stage.

These target materials are those of which the presence is looked for in the analyzed object. These target materials for instance may be explosives or drugs.

The processing system 26 determines as many projection functions as there are reference materials. These projection functions form a base which is computed from the reference-material attenuation functions They are denoted $F_{p1}$, $F_{p2}$, $F_{p3}$, $F_{p4}$. To determine these projection functions, the processing system 26 firm calculates all the mutual scalar products of the attenuation functions of the reference materials. These scalar products form a positive, diagonalized, defined matrix. As a result of this diagonalization, the eigenvalues associated with mutually orthogonal eigenfunctions are determined. Any base of projection functions is determined from the base formed by the eigenfunctions. In particular, the base formed by the eigenfunctions can be used directly.

More specifically, the determination of the projection functions may be carried out for instance using a well known procedure called principal-component analysis.

Letting $AH_1$, $AH_2$, $AH_3$, $AH_4$ . . . be the reference-material attenuations functions, this method is carried out as follows: first a square matrix is drawn up of which the elements are the pairwise scalar products of the $AH_i$ functions. The scalar product is defined for instance as the canonic scalar product of the functions $$Mij = AH_i AH_j = \int AH_i AH_j du$$

the integral limits being the extreme values of the variable u corresponding to the range of energy under consideration.

it can be shown that M can be diagonalized and that one may write $$M = P^{-1}.D.P.$$

where P is the running matrix $P^{-1}$ is the inverse matrix of P and D is diagonal matrix associated with M. The eigenvectors of M are represented by the columns of the Ps and are orthogonal.

the projection functions $F_{p1}$, $F_{p2}$, $F_{p3}$, $F_{p4}$ are obtained by linear combinations of the $AH_j$ functions of which the coefficients are the coordinates of the eigenvectors of M, that is they are the columns of the matrix P.

and it is easily shown that the base formed from the $F_{p1}$, $F_{p2}$ . . . is a orthogonal base.

The projection functions are stored in a memory of the system 26.

The attenuation functions of the target materials are projected onto the base, that is onto the projection functions. For each target material, the processing system 26 then determines a set of four values t1, t2, t3, t4 which are equal to the different projection coefficients. Letting $Att_T$ be the attenuation function of a target material, the following relation ensues $$Att_T = t_1 F_{p1} + t_2 F_{p2} + t_3 F_{p3} + t_4 F_{p4}.$$

Like all attenuation functions determined by the procedure described earlier, the attenuation function $Att_T$ way be written as the product of a unit function $Att_T$ corresponding to a unit-mass thickness of 1 g/cm² multiplied by the unit-mass thickness e with units of g/cm² of the material under consideration, namely $$Att_T = e \times (unit) Att_T.$$

It is clear that in the same manner, the coefficients t1, t2 . . . can be stated as $$t1 = e \times (unit) t_1$$

$$t2 = e \times (Unt) t_2.$$

Because thickness can be estimated only with difficulty, the four projection-determined coefficients are used to calculate three independent thickness coefficients hereafter called comparison coefficients.

The eigenvalues which were calculated to determine the projection functions are sorted in decreasing order. Illustratively the comparison coefficients are obtained from the quotients of the projection coefficients t2, t3, t4 over the coefficient t1 corresponding to the projection onto the projection function associated with the largest eigenvalue.

It is understood that these ratios are independent of the material thicknesses. They are stored in the memory of the processing system 26.

The objects to be analyzed are placed on the conveyor 28 (FIGS. 1 or FIG. 3) and move, within the x-ray beam. The speed of the conveyance means is about 15 cm/s. At a fixed frequency, for instance 100 Hz, the detectors of the strip 20 will emit a signal proportional to the intensity transmitted by the object. Thus, column by column, with one line corresponding to all the strip, the processing system 26 determines at each object point an attenuation function in u.

Next the processing system 26 carries out a projection of the attenuation function at each object point onto the base of the projection functions. Accordingly four projection coefficients are calculated at each object point.

If $Att_O$ is the object's attenuation function, then the following relation exists at one object point:

$$Att_O = a_1 F_{p1} + a_2 F_{p2} + a_3 F_{p3} + a_4 F_{p4}$$

where a1, a2, a3, a4 represent the projection coefficients at the point under consideration.

In a manner similar to the calculation of the target-material projection coefficients, the comparison coefficients are determined from the set $(a_1, a_2, a_3, a_4)$. For that purpose the processing system 26 illustratively forms the ratios $a_2/a_1$, $a_3/a_1$, $a_4/a_1$ which are coefficients independent of the object's thickness.

Comparison means consisting of the processing system 26 compare the objects set of comparison coefficients for each object point with the target material's sets of comparison coefficients. The presence of the target material in the object's constitution at that point in the object is inferred from that comparison when the values of the comparison coefficients are mutually close.

The above description applies when the analyzed object is homogeneous. But in the general case the objects rarely are homogeneous: if the object is luggage inspected for explosives, then this object is constituted of so-called discrete bodies. The measured attenuation functions therefore correspond to the attenuation of the stack but not to a discrete body.

FIG. 4 schematically shows luggage 1 containing two superposed discrete bodies 2 and 3. The luggage evinces an attenuation Al, the objects 2 and 3 resp. attenuations A2 and A3.

It is clear from FIG. 4 that when measuring transmission, the luggage alone evinces an attenuation Al, the superposition of luggage and object 2 leads to attenuation A1+A2 and the superposition of luggage and the object alone leads to attenuation A1+A3 and the superposition of luggage, object 1 plus object 2 leads to an attenuation A1+A2+A3. As a result, instead of detecting three objects (luggage, object 2, object 3), the apparatus will identify four objects of which only one evinces a specific portion with a genuine attenuation function (one part of the luggage).

To determine the attenuation of each discrete body, the invention recommends forming contour images, the expression "contour" herein meaning the transition zones between the discrete bodies, a transition zone being defined by the zone corresponding to a large change in transmitted radiation.

The expression "image" is to be construed as a table of values, each value being assigned to one pixel of the image. This image is not necessarily visuzlized by display.

The contour image may be implemented from several tables of data. For instance it may be achieved from signals emitted by the detector in response to object irradiation in the highest-energy range; but it also may be achieved following determination of the attenuation function from attenuation values at each point and at a given energy, for instance 140 Kev; moreover it may be derived from the values of the projection coefficients at each point, preferably from the most stable projection coefficient onto the function $F_{p1}$.

The contour image may be obtained from one of these data tables but advantageously several contour images will be made from several of these data tables. These images thereafter are compared one to the other and thereby spurious contour detection may be eliminated and a definitive contour image may be obtained.

This contour image is built up using image processing means 29 (FIGS. 1 and 3) which are connected to the processing means 26. This mutual segregation of the processing means 26 ad 29 is artificial and its sole purpose is simplicity of description. In fact all processing, computations, storage in memory, are implemented by one equipment, for instance a computer.

The image processing means 29 operate on the basis of data fed to them from the processing system 26. To obtain the desired contours, all known procedures may be used, for instance Soebel operators or filtering.

As already discussed, the expression "contour" denotes a transition zone, that is a band of several pixels, for instance five pixels, which follow lines defined by the selected algorithm. FIG. 5 is a partial view of the portion 40 of the object of FIG. 4 as defined by image processing. The shaded zone 5 is the transition zone.

Once the definitive contour image has been obtained, it is related to the sets of projection coefficients for each object point. Changes in object projection-coefficients are determined in the transition zones by the processing system 26. The word "changes" here denotes any modification or gradual alteration of the projection coefficients or a combination of such coefficients along a selected direction in the transition zone.

Advantageously this direction is perpendicular to the main line 6 of the contour 5, the main line being defined by the line of points where the change in transmitted radiation is a maximum for the zone under consideration.

Presently an illustrative determination of changes affecting the set of projection coefficients of points p1, p2, p3, p4, p5 intersecting the transition zone perpendicularly to the line 6 will be described.

The transition zone 5 shown in FIG. 5 separates the end constituted by the luggage from the object 3. When determining attenuation functions on either side of the contour, the attenuation function denoted Al corresponding to the luggage and the attenuation function A1+A3 corresponding to the superposition of luggage and object 3 (but not the attenuation function of the object 3 alone) are derived.

The processing system 26 uses a gradient method to determine the attenuation of the object 3 per se. Calculations indeed are carried out on the projection coefficients of the attenuation functions. While this procedure is being described for only one projection coefficient, it is obvious that it can be applied for each projection coefficient of the set of projection coefficients which is determined by each point.

The processing system 26 subtracts projection coefficient at the point p1 from the projection coefficient at the point p3. Letting $a_{11}$ be the projection coefficient at the function $F_{p1}$ at point p1, and if $a'_{13}$ is the projection coefficient on $F_{p1}$ at the point p3, then the subtraction yields the projection coefficient $a_{13}$ of the attenuation function $A_3$ alone at the function $F_{p1}$.

By repeating this operation with all projection coefficients at all points of the transition zone, the processing system determines the attenuation-function projection coefficients of each discrete body. Said system derives comparison coefficients by taking the ratios of the projection coefficients to that corresponding to the projection onto the projection function $F_{p1}$. These comparison coefficients are compared with the comparison coefficients of the target materials. It is then inferred from this comparison whether there is presence or absence of a target material in the constitution of the discrete body being checked.

Accordingly the method of the present invention allows isolating each discrete body and it determines comparison coefficients in the identification of a target material in the constitution of the discrete bodies.

Be it noted that in the discussed embodiment, the search is for transitions between the discrete bodies. In case a transition is observed toward a discrete body comprising a target material in its constitution, the comparisons between comparison coefficients are extended to the full inside of the contour or at least to an expanded zone around the contour. In this manner the isolated detections of target materials are eliminated as being false alarms. For all specific information, for instance for each set of projection coefficients of the overall object a table of values will be set up. Each of these value tables may be the base for making an image. Thanks to these tables one or more images may be visualized by displays 36 comprising a checkout monitor 40 (FIG. 1).

These displays are fitted with processing means 38 allowing zooming at will any image portion or changing the contrast or undertaking any other conventional image processing. The contour image also may be visualized alone or superposed on another image. The means 36 and 38 already are presently used in x-ray imaging and therefore will not be described further in detail.

The image points at which a target material is part of the object's constitution may be shown in the displayed image by color visualization or by blinker display. Also the detection of a target material may trigger an acoustic alarm or the display of a particular message on the checkout screen 40.

We claim:

1. A method for identifying at least one specific target material in the constitution of an object (1),
characterized in that it comprises the following stages:
    A. Previously determining the attenuation function across a wide x-ray spectrum of at least two reference materials and therefrom deriving base-forming projection functions ($F_{p1}, F_{p2} \ldots$),
    B. During a second preliminary stage, deter the attenuation of at least one target material across said x-ray spectrum and projecting the attenuation function of each target material onto said base,
    C. For each point of the object (1),
        determining the attenuation function of the object (1) for said x-ray spectrum,
        projecting the attenuation function of the object (1) onto said base
        comparing the projections so obtained with the projections from each target material and deducing from this comparison whether at least one target material is pant of the constitution of the object (1) at the point being tested.

2. Method defined in claim 1, characterized in that the x-ray spectrum evinces a range between at least 30 Kev and 100 Kev.

3. Method defined in claim 1, characterized in that the objects attenuation function, further the reference-material attenuation functions and the target-material test functions all are expressed in terms of an independent variable u bijectively related to the energy E of the x-rays.

4. Method defined in claim 3, characterized in that the variable u is selected to be the attenuation value of a fixed thickness of a calibration material (18).

5. Method defined in claim 4, characterized in that the calibration material evinces an effective Z in a range from 5 to 26.

6. Method defined in claim 1, characterized in that the projection functions are mutually orthogonal.

7. Method defined in claim 6, characterized in that the projection functions are eigenfunctions associated with eigenvalues determined by diagonalizing a matrix constituted by the scalar products of the reference-material attenuation functions.

8. Method defined in claim 7, characterized in that during a preliminary stage and for each target material, a set of projection coefficients resulting from the projection of the target-material attenuation functions onto said base is determined, said eigenvalues being arranged in decreasing order, in that a set of comparison coefficients for the target materials is derived from each set of projection coefficients by dividing each projection coefficient of the set under consideration by the coefficient of the particular set corresponding to the projection onto projection function associated to the largest of the eigenvalues, these sets of comparison coefficients for the target materials being used in comparisons allowing inferring whether at least one target material is part of the constitution of object (1).

9. Method defined in claim 8, characterized in that, because the inspected object is constituted of discrete bodies (1, 2, 3),
    an image is made of the contours (5) of the discrete bodies, said contours (5) being transition zones between the different discrete bodies,
    for each point of the object (1), a set of projection coefficients resulting from the projection of the attenuation function of the object onto said base is determined,
    variations in the sets of projection coefficients of object inside the transition zones (5) are determined, and
    from said variations, comparison coefficients with the comparison coefficients of the target materials are derived.

10. Method defined in claim 1, characterized in that the effective atomic numbers of the reference materials are regularly spaced in a range from 3 to 30.

11. Method defined in claim 10, characterized in that a first reference material is selected from the materials evincing an effective atomic number in a range from 3 to 7, in that a second reference material is selected from the materials evincing an effective atomic number in a range from 7 to 10, in that a third reference material is selected from the materials evincing an effective atomic number in a range from 10 to 17 and in that a fourth reference material is selected from among the materials evincing an effective atomic number in the range from 17 to 30.

12. Method defined in claim 11, characterized in that at least one of the reference materials is selected as follows: the first reference material is polyethylene, the second reference material is PTFE, the third reference material is duralumin, the fourth reference material is iron.

13. Method defined in claim 1, characterized in that the target materials are explosives and/or drugs.

14. Apparatus implementing a method defined in claim 1, characterized in that it comprises:
    means (10, 12, 16, 17, 18, 20 or 30) determining attenuation functions across a wide x-ray spectrum, said attenuation functions being expressed in terms of an independent variable u which is bijectively related to the energy of the x-rays.
    processing means (26) able to project attenuation functions onto functions forming a base and previously determined from the attenuation functions of at least three reference materials.

conveying means (28) for an object (1) to be analyzed, said conveying means allowing to expose said object to the attenuation-function determining means, comparison means (27) comparing the object's attenuation-function projection with previously implemented attenuation-function projections of at least one target material, in order to infer from this comparison whether at least one target material is present in the object constitution, displays (36) to display at least one object image by distinguishing the points at which a target material is present in the object constitution.

15. Apparatus defined in claim 14, characterized in that it furthermore comprises image-processing means (29) able to geometrically isolate each object substance to form a contour image.

16. Apparatus defined in claim 14, characterized in that the attenuation-function determining means comprise a calibration-material component (18) and evince different thicknesses, said component (19) being displaceable at will into the x-ray beam (14, 15).

17. Apparatus defined in claim 14, characterized in that the attenuation-function determining means comprise a source (10, 12, 16, 17) emitting an x-ray beam in sequence in several spectral ranges and further comprise a strip (20) of detectors (22), each detector (22) responding to all the spectral ranges.

18. Apparatus defined in claim 14, characterized in that the attenuation-function determining means comprise an x-ray beam generator (32, 34) with a wide and fixed spectrum and a strip (20) of stacked detectors (30), each detector (30a, 30b . . . ) of a stack acting as a high-pass filter for the adjacent and following detector.

* * * * *